US006618957B2

(12) United States Patent
Novak et al.

(10) Patent No.: US 6,618,957 B2
(45) Date of Patent: Sep. 16, 2003

(54) METHOD AND APPARATUS FOR MICROWAVE UTILIZATION (76) Inventors: John F. Novak, 34 N. Chestnut St., Fredericktown, OH (US) 43019; Michael R. Burch, 11999 Woodview La., Fredericktown, OH (US) 43019

( * ) Notice: Subject to any disclaimer, the term of this patent is extended or adjusted under 35 U.S.C. 154(b) by 0 days.

(21) Appl. No.: 09/930,533

(22) Filed: Aug. 15, 2001

(65) Prior Publication Data
US 2002/0046474 A1 Apr. 25, 2002

Related U.S. Application Data
(60) Provisional application No. 60/225,701, filed on Aug. 16, 2000.

(51) Int. Cl.[7] .................................................. F26B 3/34
(52) U.S. Cl. ............................ 34/264; 34/259; 34/265; 34/487; 34/519
(58) Field of Search .......................... 34/259, 245, 263, 34/264, 265, 402, 418, 443, 487, 519, 201

(56) References Cited

U.S. PATENT DOCUMENTS

| | | | |
|---|---|---|---|
| 4,055,001 A | * 10/1977 | Forster et al. ................. 34/264 |
| 4,087,921 A | 5/1978 | Blok |
| 4,126,945 A | 11/1978 | Manser et al. |
| 4,160,145 A | 7/1979 | Rueggeberg |
| 4,193,869 A | 3/1980 | Brucker et al. |
| 4,234,775 A | 11/1980 | Wolfberg et al. |
| 4,242,220 A | 12/1980 | Sato |
| 4,446,348 A | 5/1984 | Huang et al. |
| 4,567,340 A | * 1/1986 | Latchum, Jr. ................ 219/701 |
| 4,570,045 A | 2/1986 | Jeppson |
| 4,592,291 A | * 6/1986 | Sullivan, III ................ 110/346 |
| 4,665,101 A | 5/1987 | Ficker |
| 4,746,968 A | 5/1988 | Wear et al. |
| 5,105,563 A | * 4/1992 | Fingerson et al. ............ 34/203 |
| 5,152,074 A | * 10/1992 | Kishi .......................... 34/247 |
| 5,237,755 A | * 8/1993 | Lowe ........................... 34/255 |
| 5,270,000 A | 12/1993 | Goldner et al. |
| 5,335,425 A | 8/1994 | Tomizawa et al. |
| 5,373,646 A | * 12/1994 | Wosnitza et al. ............. 34/256 |
| 5,634,281 A | * 6/1997 | Nugent ........................ 34/207 |
| 5,864,964 A | * 2/1999 | Barragan ..................... 34/212 |
| 5,950,325 A | * 9/1999 | Mehdizadeh et al. ........ 34/256 |
| 5,974,687 A | * 11/1999 | Gante et al. ................. 34/265 |
| 6,004,590 A | 12/1999 | Subramaniam et al. |
| 6,025,580 A | 2/2000 | Yagi |
| 6,128,831 A | 10/2000 | Durance et al. |
| 6,233,841 B1 | * 5/2001 | Beach .......................... 34/262 |
| 6,247,246 B1 | 6/2001 | Scalese et al. |
| 6,297,479 B1 | 10/2001 | Wefers |

OTHER PUBLICATIONS

International Search Report regarding PCT/US01/25564.
Written Opinion regarding PCT/US01/25564.
International Preliminary Examination Report regarding PCT/US01/25564.

* cited by examiner

*Primary Examiner*—Ira S. Lazarus
*Assistant Examiner*—Andrea M. Ragonese
(74) *Attorney, Agent, or Firm*—Buckingham, Doolittle & Burroughs, LLP; Louis F. Wagner (57) ABSTRACT

The invention described herein pertain generally to a process for drying and/or pathogen reduction as well as an apparatus effective for the same, the process comprising the steps of feeding a sample containing water onto a mesh conveyor belt; transporting the sample into a heated chamber having an air flow about, around and through the sample; exposing said sample to at least two sources of microwaves in non-parallel alignment to each other; and collecting the sample. The at least two sources of microwaves are from a split waveguide assembly, producing microwaves which are essentially 90° out of phase to each other. The heated chamber is between approximately 75° C. and 125° C. The convection heating supplements the microwave heating thereby both heating the sample from the outside in and also from the inside out. The microwave frequency is between 915 MHz and 1000 MHz, preferably approximately 915 MHz.

36 Claims, 7 Drawing Sheets

METHOD AND APPARATUS FOR MICROWAVE UTILIZATION

This application claims the benefit of provisional application Ser. No 60/225,701 filed Aug. 16, 2000.

TECHNICAL FIELD

The invention described herein pertains generally to a method and apparatus for drying and sterilizing (pathogen reduction) organic materials, e.g., paper, municipal sewage treatment, grain, and in a second embodiment, depolymerizing polymeric-based materials, e.g., plastics, including crosslinked plastics and rubber-based polymers, including crosslinked rubbers such as sulfur-based crosslinks as used in tires. These organic materials are dried by the direct application of bifurcated out-of-phase microwave energy to the organic materials and convection of combustion products derived from natural gas/liquefied petroleum gas (LPG) through the organic materials, resulting in a reduced moisture content product in one application. A decrosslinked, and at least partially depolymerized product is achieved without convection of combustion products in a second application.

BACKGROUND OF THE INVENTION

In the field of moisture reduction, escalating costs of natural gas and liquefied petroleum gas are of increasing concern to those involved in the commercial drying of organic materials in paper mills, municipal sewage plants and grain drying plants. With the inherent aging of the facilities, coupled with escalating energy and capital equipment costs, the refurbishing and replacement costs of these plants becomes increasingly difficult to justify. Many efforts to substantially improve throughput efficiency or reduce energy costs have failed to meet their objectives, either from an economic or technical point of view.

In the field of pathogen reduction, there are six alternatives for meeting Class A pathogen requirements pursuant to United States Regulations, 40 CFR, Part 503. These are:

Alternative 1: Thermally Treated Biosolids wherein the biosolids are subjected to one of four time-temperature regimes;

Alternative 2: Biosolids Treated in a High pH—High Temperature process;

Alternative 3: Biosolids Treated in Other Processes wherein it can be demonstrated that reduced enteric values and viable helminth ova values can be achieved;

Alternative 4: Biosolids Treated in Unknown Processes—wherein biosolids can be tested for pathogens salmonella, fecal coliform bacteria, enteric viruses, and viable helminth ova;

Alternative 5: Biosolids Treated in a Process to Further Reduce Pathogens (PFRP); or Alternative 6: Biosolids Treated in a Process Equivalent to a PFRP.

For all of the alternatives listed above, one of two product criteria must be met. Either the density of fecal coliform in the biosolids must be less than 1,000 most probable numbers (MPN) per gram total solids (dry weight basis) or the density of Salmonella bacteria in the biosolids must be less than 3 MPN per 4 grams of total solids (dry weight basis). Either of the above criteria must be met at one of the following times: when the biosolids are used or disposed; when the biosolids are prepared for sale or give-away in a bag or other container for land application; or when the biosolids or derived materials are prepared to meet the requirements for EQ biosolids.

There are four time-temperature regimes for Class A Pathogen Reduction under Alternative 1.

| Regime | Applies to: | Requirement | Time-Temperature Relationship(1) |
|---|---|---|---|
| A | Biosolids with 7% solids or greater (except those covered by Regime B) | Temperature of biosolids must be 50° C. or higher for 20 minutes or longer | $D = \dfrac{131,700,000}{10^{0.14t}}$ |
| B | Biosolid with 7% solids or greater in the form of small particles and heated by contact with either warmed gases or an immiscible liquid | Temperature of biosolids must be 50° C. or higher for 15 seconds or longer | $D = \dfrac{131,700,000}{10^{0.14t}}$ |
| C | Biosolids with less than 7% solids | Heated for at least 15 seconds but less than 30 minutes | $D = \dfrac{131,700,000}{10^{0.14t}}$ |
| D | Biosolids with less than 7% solids | Temperature of sludge is 50° C. or higher with at least 30 minutes or longer contact time | $D = \dfrac{131,700,000}{10^{0.14t}}$ |

(1) D = time in days; t = ° C.

For all of the four time-temperature regimes for Class A Pathogen Reduction, the microwave thermal process exceeds all specifications of Regimes (A–D) for biosolids with 7% solids or greater, which indicates a minimum exposure of 15 seconds or longer at 50° C.

SUMMARY OF THE INVENTION

In accordance with the present invention in one aspect, there is provided a combined microwave/convection heating, e.g., natural gas, liquefied petroleum gas, ceramic resistance heating, etc., process to more economically produce organic materials suitable for reuse in the agricultural and consumer markets within a specified and controlled moisture content range, as well as reduced pathogens and odor. The invention provides a process for the reduction of moisture content, pathogens and odor from paper mill pulp sludge, sewage treatment plant sludge and grains, the process comprising the direct application of microwave energy to the organic materials with simultaneous convection heating by natural gas/LPG combustion products through the organic materials, resulting in moisture, pathogens, and odor reduction in a predictable, precise, controlled manner.

With biosolids, the process involves the use of microwaves to penetrate the biosolids and in doing so, excite the water molecules, which create heat within milliseconds up to 106° C. The microwaves transmitted by each magnetron are rated at a frequency of 915 MHz, with frequencies of this magnitude attacking the single cell pathogens, creating an environment that literally destroys or structurally causes the pathogens to explode. This environment is controlled in the 375 KW microwave thermal chamber/applicator with a variable speed belt for a period of not less than 18 seconds and not more than 30 minutes.

It has been determined that the natural gas/LPG combustion products, which are produced as a direct result from injection into a gas burner and ignited, may also be produced from direct injection of the natural gas/LPG into the combustion chamber of an aero-derivative gas turbine, whose combustion products may be passed through the organic material and subsequently recovered in a combined cycle application for the production of electricity, steam or other waste heat application. The gas turbine is coupled to an electrical generator, which provides electrical power for this invention. It has also been determined that the moisture driven from the products can be: directed into a vapor compressor for the production of high pressure saturated steam and returned to the plant to supplement steam production from an existing boiler; directed into a heat exchanger or condenser for the production of hot water and returned to the plant for plant utility use; directed into a chiller for the production of refrigeration; or directly injected into the combustion chamber of a fired boiler or gas turbine for reduction of carbon monoxide (CO) or nitrogen oxides (NOX). Any or all of these methods of utilization of recovered moisture further contributes to improved economics.

It is an object of this invention to overcome the limitations of the prior art and to provide a means of drying organic materials much more efficiently, sterilize the organic materials, and reduce unpleasant odors, along with reduced energy and capital costs.

It is another object of this invention to provide an improved method for decrosslinking polymers using both microwave and radiant convection energy.

It is still another object of this invention to provide an improved method for depolymerizing polymers using both microwave and radiant convection energy.

It is yet another object of this invention to provide an improved design for the microwave distribution within the chamber.

It is still yet another object of this invention to be portable for demonstration of the above methods to a potential customer at a paper pulp mill, sewage treatment plant or scrap tire facility without additional equipment.

It is additionally an object of this invention to overcome the limitations of the prior art and to provide a means of meeting Class A pathogen requirements.

It is additionally another object of this invention to provide a means of exceeding class A pathogen requirements by a total pathogen kill.

These and other objects of this invention will be evident when viewed in light of the drawings, detailed description, and appended claims.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION OF THE INVENTION

In the following description, similar features in the drawing have been given similar reference numerals. In the drying application, organic material received from paper mills, sewage treatment plants and grain drying plants may be introduced into the microwave-based natural gas/LPG-assisted plant. The organic material from a paper mill is typically directly discharged from a belt press in the form of treated or untreated, primary or secondary, paper pulp sludge with a moisture content from 75–89% into an optional hopper, with a coarse auger to produce more homogeneous particle sizes and a more uniform distribution on the input to the shaker table. Organic material received from sewage treatment plants is typically directly discharged from a belt press in the form of treated or untreated sewage sludge with a moisture content from 75–89% into an optional hopper, with a coarse auger to produce more homogeneous particle sizes and distribution on the input to the shaker table. Grains received from local agricultural collection centers with a typical moisture content of 30–40% may be directly discharged into an optional hopper, with a coarse auger to produce more homogeneous distribution on the input to the shaker table.

Figure 1:
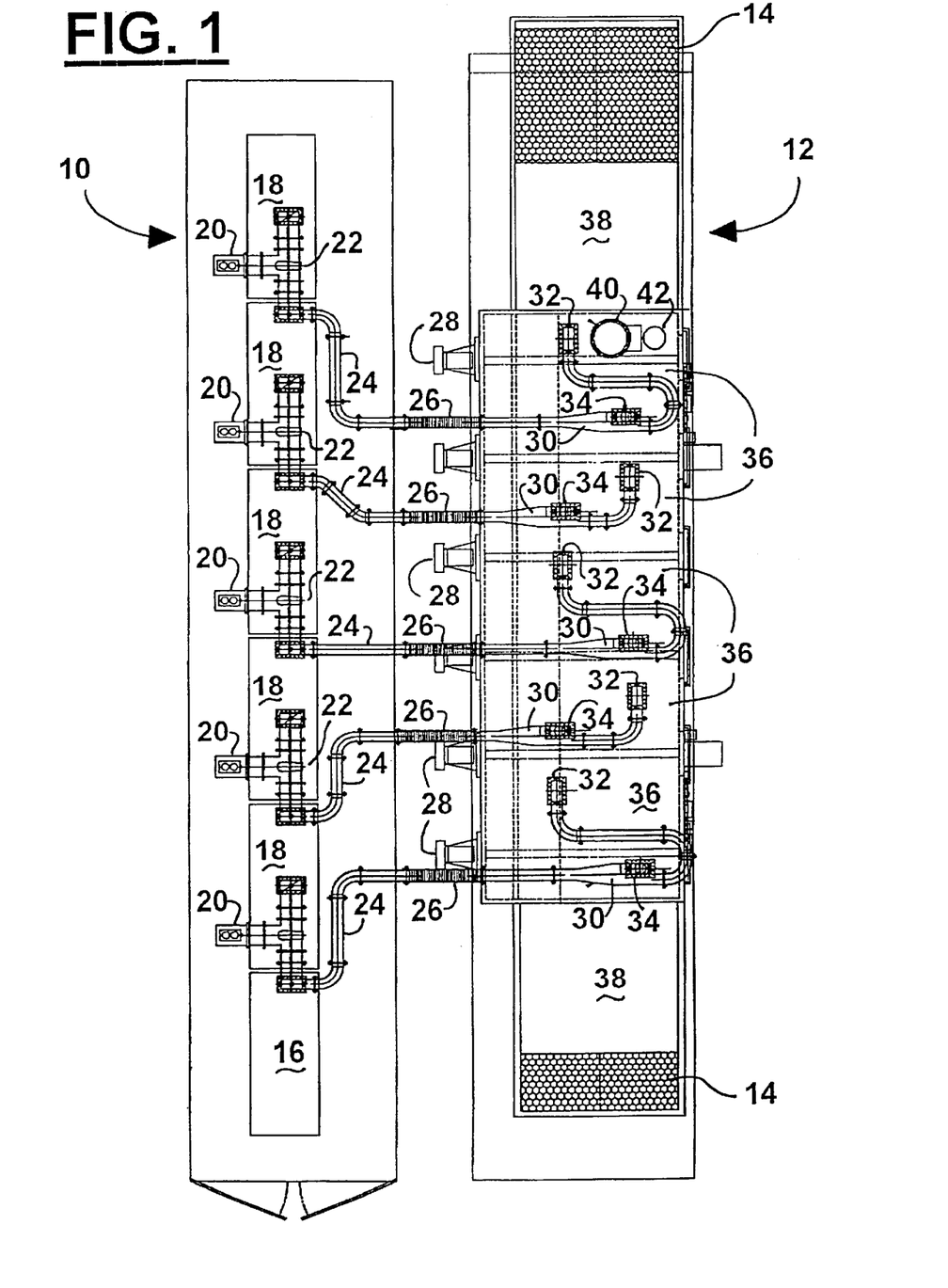
FIG. 1 is a top plan view of a microwave-based gas assisted dryer assembly drawing showing a microwave generator and a microwave applicator housed within a movable trailer.

As illustrated in FIG. 1, the apparatus comprises two main elements: (1) a portable microwave-based gas-assisted dryer assembly 12 coupled to a portable microwave generator 10. Material which is to be dried, typically organic material, is deposited upon open mesh continuous conveyor belt 14 of microwave applicator 12. Within the portable microwave generator are illustrated five microwave generators 18 in electrical communication and controlled by main control panel 16. Each microwave generator has a magnetron 20 and a microwave circulator 22. The generated microwaves move from the generator 10 to the dryer assembly 12 via waveguides 24 which may include flexible accordion-like waveguides 26. In the particular dryer assembly shown in FIG. 1, six radial inflow circular fans are illustrated 28 with an assembly exhaust fan 40 with associated motor 42. Each waveguide contains a microwave splitter 30 which directs the microwave in into microwave chambers 36 in a direction colinear 32 with the longitudinal plane of the conveyor belt 14 and normal 34 to this same longitudinal plane. Microwave leakage outside of the chambers 36 is eliminated by R.F. traps 38 (choke pin type).

Figure 2:
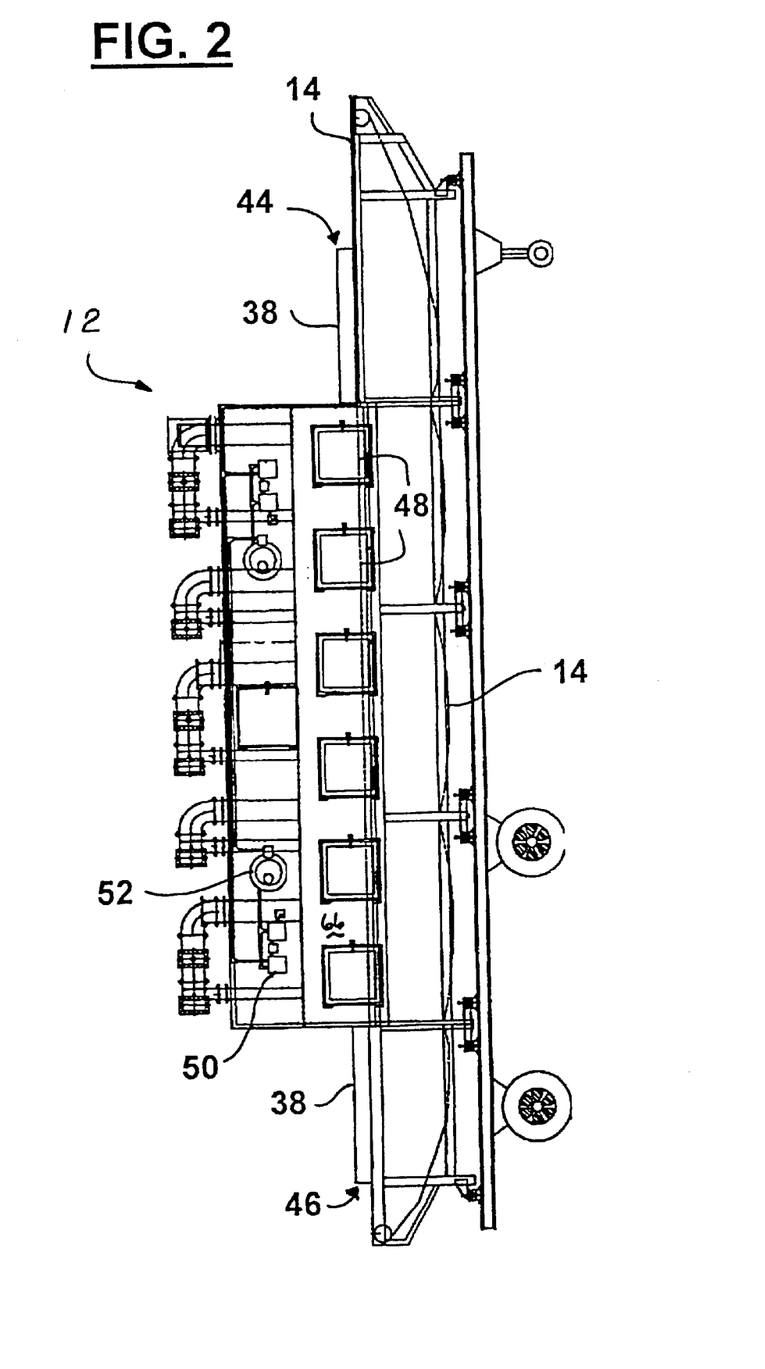
FIG. 2 is a side plan view of the microwave applicator trailer showing continuous web belt.

As illustrated in FIG. 2, the microwave-based gas-assisted dryer has one entry port 44 and one exit port 46 which are in longitudinal communication with open mesh continuous conveyor belt 14, said belt being of mesh composition and having longitudinal raised sides for retention of the sample, said sides typically being approximately 2" (5.08 cm) in elevation. As illustrated, there are six access viewing ports 48 positioned on a side of the microwave applicator 12. Illustrated in FIGS. 1 and 2 are multiple microwave applicators 36 which are interconnected to form a tunnel. While a total of five applicators are shown, there is no need to limit the invention to such and both larger and smaller numbers of chambers are envisioned to be within the scope of the invention. In fact, the invention operates with just one applicator chamber. The microwave energy is transferred from the microwave generator 10 to the applicator via a waveguide 24, often with accordion-like bends 26 to meet the physical geometries imposed on any system, and exits the same via a waveguide splitter 30. The source of the microwave energy in the generator is a magnetron, which operates at frequencies which range from 915 megaHertz (MHz) to 2450 MHz, more preferably from 915 MHz to 1000 MHz, and most preferably at approximately 915 MHz +/−10 MHz. The lower frequencies are preferred over the more common frequency of 2450 MHz typically used in conventional microwave ovens due to increased magnetron power, availability and penetration depth into the organic material at 915 MHz, along with an increase in operating efficiency from 60–88%. Each magnetron has a separate microwave generator control panel in electronic communication with a main control panel for system control.

Figure 3:
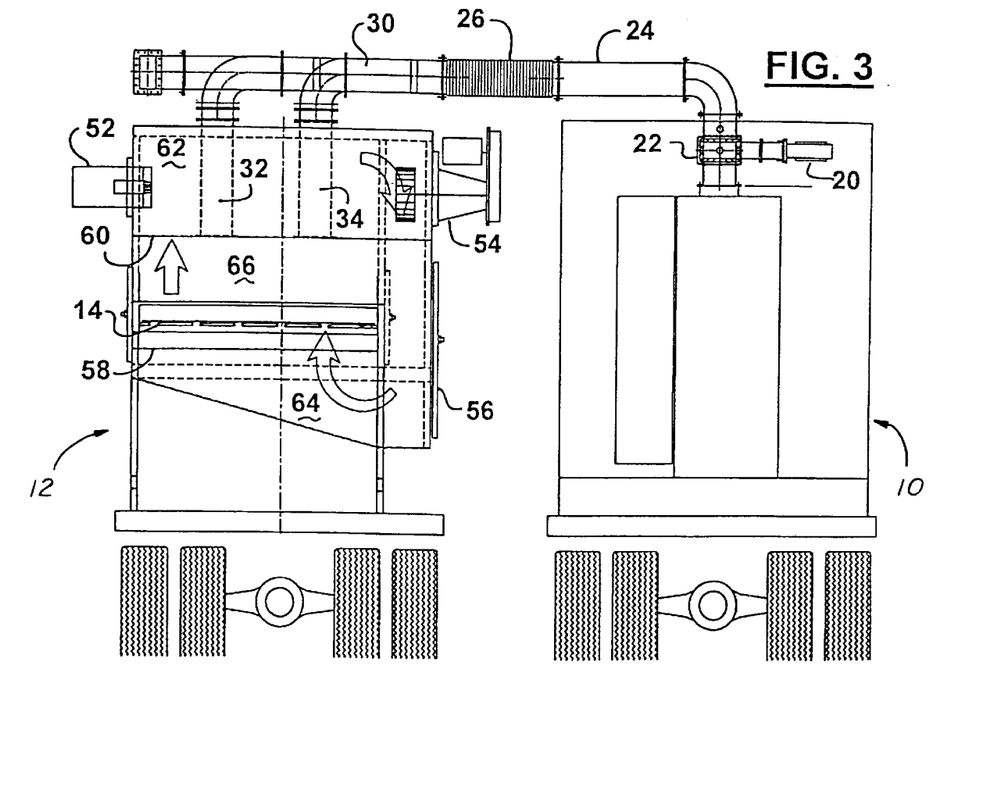
FIG. 3 is a rear plan view of the assembly of FIG. 1.

As shown in FIG. 3, this microwave applicator has an upper chamber 62 an active middle chamber 66 and a lower chamber 64, the chambers separated by upper and lower perforated screens 60 and 58 respectively. For the application described in this invention, the active applicator height is 34⅜" (87.3 cm), although it is well known how to appropriately size the active area. The directional arrows are present to facilitate an understanding of the air flow when the gas-assisted mode of operation is utilized. Blower motor 54 provides downward velocity to the air within the plenum which egresses with upward direction through lower perforated screen 58, open area mesh belt 14 and upper perforated screen 60. The gas is heated through utilization of gas burner 52 capable of providing 400,000 BTU.

Figure 4:
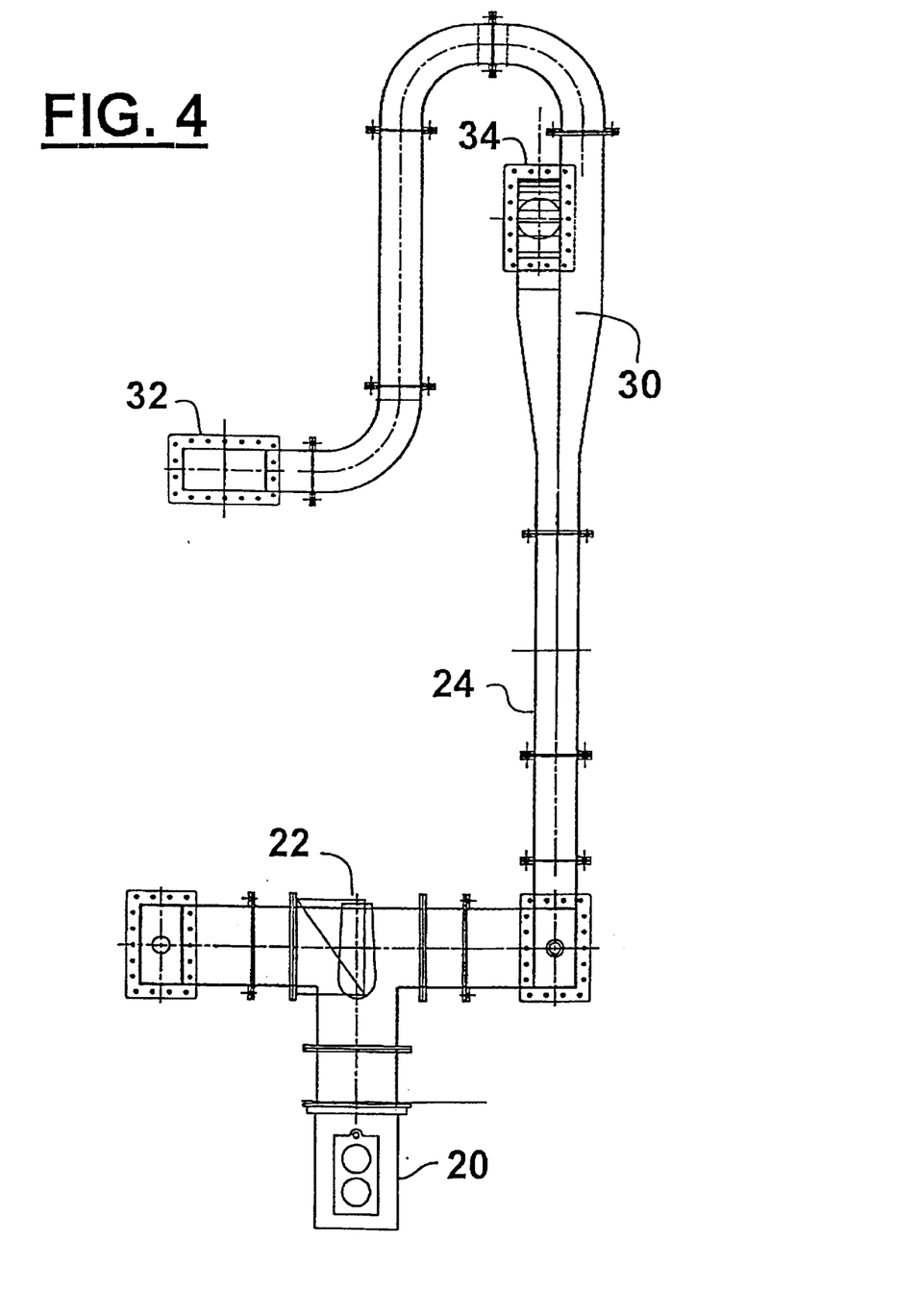
FIG. 4 is an enlarged top view of a bifurcated waveguide.

In the event that the microwave energy is not absorbed by the organic material, a condition which results in reflected energy, this reflected microwave energy is absorbed by a device known as a circulator. The circulator is sized to absorb 100% of the microwave energy generated by the magnetron to prevent damage to and destruction of the magnetron. Each microwave generator transmits its energy via a waveguide into the series-connected chambers or applicator. In a preferred embodiment, each microwave generator operates at a center frequency of 915 MHz +/−10 MHz. In expanded view shown in FIG. 4, this microwave energy is coupled from the microwave generator, through a splitter 30, into the applicator via two waveguides 32,34 which serve as rectangular conduits into each applicator cavity 36.

The waveguide entry to the applicator is via a three-ported splitter, which splits the electromagnetic wave of microwave energy prior to the two-plane entry into the top of the applicator, while maintaining electric field dominance. The waveguide inputs from the splitter are in the same plane at the top of the applicator, but one plane is oriented along the x-axis, while the other plane is oriented along the y-axis. The split waveguide assemblies are designed so as to produce microwaves which are essentially 90° out of phase. This results in the generation of multiple modes of microwave energy within the applicator and elimination of the requirement for mode stirrers, while providing a more uniform distribution of the microwave energy throughout the applicator.

The microwave energy is produced by the generator and transmitted into a WR 975 standard rectangular waveguide. When portable units are desired, with the generators mounted on one trailer and the applicator is mounted on an adjacent trailer, the waveguide coupling between the two trailers is accomplished with a ribbed, flexible waveguide, as shown in the attached drawings. At the output of the flexible waveguide, the microwave energy enters a bifurcated waveguide. One output connects to a right angle waveguide section, from which the microwave energy enters directly into the chamber. The other output is presented to a two-section long-radius, right angle waveguide section, which accomplishes the turning of the microwave energy path 180°, while maintaining electric field dominance. The microwave energy enters a short straight section and another long radius, right angle waveguide section. The microwave energy is then coupled into a right angle waveguide section and enters directly into the chamber. Although the waveguide entries into the applicator are in the same plane at the top of the applicator, the orientation of the two waveguide entries, relative to the centerline of the applicator, is 90° to each other. One waveguide entry section to each applicator entry point is parallel to the flow of the organic material, while the other is perpendicular to the flow of the organic material. The other significant feature of this design is that the distance from the output from the bifurcated waveguide, which couples the microwave energy to the applicator entry port parallel to the flow of the organic material, is physically much longer than the output feeding the perpendicular port. This additional length results in a different characteristic impedance at the chamber entry point, a time delay in the microwave energy reaching the applicator entry point, and a relative phase shift in the energy wave itself. As stated previously, the generator operates at a nominal center frequency of 915 MHz, with an allowable variation of +/−10 MHz. At this frequency, the effects of additional waveguide lengths and bends present a very noticeable change in the time/phase relationships due to the impedance mismatch. However, in this invention, the impedance mismatch, along with the frequency of operation is a significant contribution to the microwave energy mixing within the applicator, allowing more even energy distribution throughout the entire cavity.

Since the applicator is open at both ends to admit and discharge organic material, the microwave energy could propagate into the surrounding area, resulting in radio frequency (RF) interference and a hazard to personnel. To prevent leakage of the microwave energy from the applicator, a device known as an RF trap 38, containing a matrix of grounded ¼—wavelength RF stubs (antennae), with ¼—wavelength spacing between the RF stubs, installed at each end of the applicator to insure attenuation of microwave energy for compliance with leakage specifications of <10 mW/cm$^2$ maximum for industrial applications and <5 mW/cm$^2$ maximum for food applications.

The active area in the microwave applicator typically consists of a rectangular cavity, measuring 24'(7.31 m) by 6' (1.82 m) by 3' (0.91 m) designed specifically for the microwave energy coupled from five microwave generators (shown in FIG. 1) and five waveguide splitter assemblies, which results in ten sources of microwave energy to the applicator cavity and more uniform distribution. The applicator also contains a continuous, self-aligning, porous, 6' (1.82 m) wide polypropylene belt with 2" (5.08 cm) material retaining sides and 24–28% open area, an RF trap at each end containing a matrix of grounded ¼—wavelength RF stubs, ductwork admitting the products of combustion from two gas burners, six circulating blowers to force the heated air through the belt and material and one exhaust blower to remove the moisture to the outside atmosphere. Makeup air for the burners is provided by an eternally-mounted blower, which is part of the overall burner assembly. The temperature of the heated air is controlled by a set point controller preset at 220° F. (104.4° C.), the temperature sensor being positioned within the circulating air plenum chamber.

The cavity also contains an exhaust duct for the moisture and heated air to escape to the atmosphere. The five microwave generators consist of five magnetrons, each rated at 75 kW continuous power, five circulators, each capable of absorbing 100% power generated by their respective magnetrons, five switched-mode power supplies, each operating at 480 Volts, 3-phase and capable of delivering 120 amperes (amps) to each magnetron, and five power transformers. The only additional requirement is cooling water in the amount of 4 gal./min. (15.14 L./min.) per magnetron and 4 gal./min. (15.14 L./min.) of cooling water per circulator water load. Each microwave generator is a three-door enclosure with front and rear door access measuring 80" (2.03 m) by 32" (0.81 m) by 84" (2.13 m).

To process additional material or increase the throughput, one may add additional microwave generators, extend the applicator length, increase belt speed and increase the number of gas burners proportionally. The gas burners operate using natural gas, LPG, or combinations thereof. This invention allows the addition of microwave generators and relative appurtenances in sets of five, along with an extension of the applicator as dimensionally-defined above. The standard design, which supports the majority of organic product drying applications, contains three modules. Through careful design, this modular concept presently may be extended to include a maximum of 80 microwave generators or 16 modules, within one common applicator cavity. For small variations in the moisture content of the organic material, the belt speed may be adjusted to change the dwell time of the material in the applicator. Belt speed control is accomplished by changing the speed setpoint on the touchscreen in the Main Control Panel (MCP), adjacent to the line of five microwave generator panels.

In one aspect of the invention, the design of the unit is as a portable demonstration unit, with the microwave generators and control cabinets, along with the MCP mounted in one trailer and microwave applicator assembly mounted on an adjacent trailer.

System control is accomplished by the use of a Programmable Logic Controller (PLC) with Input/Output (I/O) modules and a Data Highway to a Remote Terminal Unit (RTU) in a main control panel. The PLC is mounted in the MCP. PLC communication modules are mounted in each microwave generator enclosure, which permits continuous bidirectional communication between the PLC and the operator interface terminal (touchscreen). The PLC program provides continuous sequencing, monitoring and control functions. The PLC program also communicates along a data highway to display alarm/shutdown status and operating parameters on the RTU. The RTU provides a real time display in both analog and digital format. The summary status touchscreen indicates power output, reflected power, anode current and voltage, filament current, magnet current, generator cabinet temperatures, applicator temperatures, internal and external water system temperatures and flow rates.

Additional magnetron protection is insured by a directional coupler circuit, which monitors the reflected power and de-energizes the high voltage to the magnetron. An arc detection system protects the magnetron, three-port circulator and waveguide by de-energized the high voltage upon detection of arcing within the applicator. Fire detection within the applicator includes infra-red (IR) sensors, smoke detection and rate-of-rise temperature detectors connected in series with the safety shutdown system. Any shutdown parameter which exceeds the preset level initiates an immediate shutdown of the high voltage system and enables the safety shutdown system to provide an orderly and controlled shutdown. The safety shutdown system includes both fail-safe hardwired circuitry and programmable shutdown logic, along with local and remote emergency stop buttons to provide maximum protection for operating and maintenance personnel and equipment. Access doors in both the generator and applicator enclosures, main power sources and the high voltage power supplies are provided with fail-safe limit switches and interlocked with the startup sequence in the PLC program and monitored during microwave operation to protect operating and maintenance personnel from exposure to microwave energy and shock hazards. Further, the applicator access doors contain slotted ¼—wavelength chokes and dual fail-safe limit switches interlocked with the PLC program to immediately (<10 mS) switch off the high voltage in the event of opening during operation. A main fused-disconnect switch is included with both keyed interlocks and mechanical lockout features. Finally, a grounded bus bar dimensioned ¼"×2" (0.64 cm×5.1 cm) is provided to insure absolute ground integrity from the customer power source to all equipment included within this invention.

This is standard PLC/hardwire ladder logic programming, depicting a Boolean expression for a series shutdown circuit, designed for failsafe operation. The emergency switches are normally closed (push to open), the low level switches must reach their setpoint before operation may be sequenced, and the high level switches will open upon exceeding their setpoint. Any open switch in this series string will cause the master shutdown relay to de-energize, which results in the de-energizing of the high voltage circuits and forces the PLC to effect an immediate and orderly shutdown sequence.

The best mode for carrying out the invention will now be described for the purposes of illustrating the best mode known to the applicant at the time. The examples are illustrative only and not meant to limit the invention, as measured by the scope and spirit of the claims.

EXAMPLE #1

A summary of recorded test data from web paper pulp, with 62% moisture, specific heat of 0.35 BTU/lb.—° F. (1465.4 Joules/kg.—° C.) and a wet density of 32.75 lbs/ft$^3$ (524.6 kg/m$^3$) is provided in Tables I–IV at varying microwave powers ranging from 5 to 45 kW using the apparatus of FIGS. 1–2. The initial sample weight was 6.8 lbs (3.1 Kg). For the purposes of this experiment, an 8' (2.4 m) applicator was employed using one variably controllable 50 kW magnetron with two parallel in-line waveguides parallel to the center line of the chamber. The chamber measured 6' (1.8 m) by 4' (1.2 m). The sample was conveyed into the applicator using a self-aligning porous 6' (1.8 m) wide polypropylene belt with 2" (5.1 cm) retaining sides and a 24–28% open mesh area having ¼"×⁵⁄₁₆" (0.64 cm×0.79 cm) diagonal spacing perforated screen mesh. Convection heating, using a set point controller at 220° F. (104.4° C.), was provided by an electrical resistance space heater supplying air to the bottom of the chamber, which was blown, both through and around the conveyor. A mode stirrer was used. A 6.8 lb. (3.1 kg.) sample of characteristics defined above was loaded onto the conveyor belt and transported into the microwave applicator, tunnel or chamber after achieving a steady-state temperature within the chamber. The conveyor belt was stopped and held in the center of the chamber for the defined number of minutes shown in Tables I–IV, the sample removed and moisture content measured.

TABLE I (5 kW Power)

| Time (min) | 0 | 5.3 | 7.3 | 9.3 | 11.3 | 13.3 | 15.3 | 17.3 | 19.3 | 21.3 | 23.3 | 25.3 | 27.3 | 29.3 | 31.3 | 33.3 | 35.3 |
|---|---|---|---|---|---|---|---|---|---|---|---|---|---|---|---|---|---|
| Moisture (wt) | 4.2 | 3.8 | 3.5 | 3.2 | 2.9 | 2.6 | 2.3 | 2.0 | 1.5 | 1.2 | 0.9 | 0.7 | 0.5 | 0.4 | 0.3 | 0.2 | 0.1 |
| % Water | 62 | 59 | 58 | 55 | 53 | 50 | 47 | 43 | 36 | 32 | 27 | 22 | 17 | 13 | 10 | 7 | 4 |
| % Solid | 38 | 41 | 42 | 45 | 47 | 50 | 53 | 57 | 64 | 68 | 73 | 78 | 83 | 87 | 90 | 93 | 96 |
| Sample Weight | 6.8 | 6.4 | 6.1 | 5.8 | 5.5 | 5.2 | 4.8 | 4.5 | 4.1 | 3.8 | 3.5 | 3.3 | 3.1 | 3.0 | 2.9 | 2.8 | 2.7 |

TABLE II

(15 kW Power)

| Time (min) | 0 | 2 | 4 | 6 | 8 | 10 | 12 |
|---|---|---|---|---|---|---|---|
| Moisture (wt) | 4.22 | 3.7 | 2.7 | 1.9 | 1.2 | 0.6 | 0.2 |
| % Water | 62 | 59 | 51 | 42 | 31 | 19 | 8 |
| % Solid | 38 | 41 | 49 | 58 | 69 | 81 | 92 |
| Sample Weight | 6.8 | 6.3 | 5.4 | 4.7 | 3.8 | 3.2 | 2.8 |

TABLE III

(30 kW Power)

| Time (min) | 0 | .5 | 1 | 1.5 | 2 | 2.5 | 3 | 3.5 | 4 | 4.5 |
|---|---|---|---|---|---|---|---|---|---|---|
| Moisture (wt) | 4.2 | 3.9 | 3.5 | 3.0 | 2.6 | 2.1 | 1.78 | 1.38 | 0.9 | 0.6 |
| % Water | 62 | 60 | 58 | 54 | 50 | 45 | 39 | 33 | 26 | 19 |
| % Solid | 38 | 40 | 43 | 46 | 50 | 55 | 61 | 67 | 74 | 81 |
| Sample Weight | 6.8 | 6.5 | 6.1 | 5.6 | 5.1 | 4.7 | 4.3 | 3.9 | 3.5 | 3.2 |

TABLE IV

(45 kW Power)

| Time (min) | 0 | .33 | .67 | 1 | 1.33 | 1.67 | 2 | 2.33 | 2.67 | 3 |
|---|---|---|---|---|---|---|---|---|---|---|
| Moisture (wt) | 4.2 | 3.9 | 3.1 | 2.4 | 1.9 | 1.4 | 1.1 | 0.8 | 0.4 | 0.2 |
| % Water | 62 | 60 | 54 | 48 | 42 | 34 | 30 | 23 | 14 | 8 |
| % Solid | 38 | 40 | 46 | 52 | 58 | 66 | 70 | 77 | 86 | 92 |
| Sample Weight | 6.8 | 6.5 | 5.6 | 5.0 | 4.5 | 3.9 | 3.7 | 3.3 | 3.0 | 2.8 |

EXAMPLE #2

A second experiment was conducted similar to that described above, except that a 40 lb. (18.1 kg.) sample was placed on the belt at the entrance to the applicator, with a belt speed setting ranging from 1–8 ft/min (0.3–2.4 m/min), based on the extrapolated drying curves obtained from Example #1. The material sizes randomly ranged from a ragged marble size to approximately 1½×2¼ inches (3.8×5.7 cm). The material met the desired value of reduction in moisture content to 15% or less.

Figure 5:
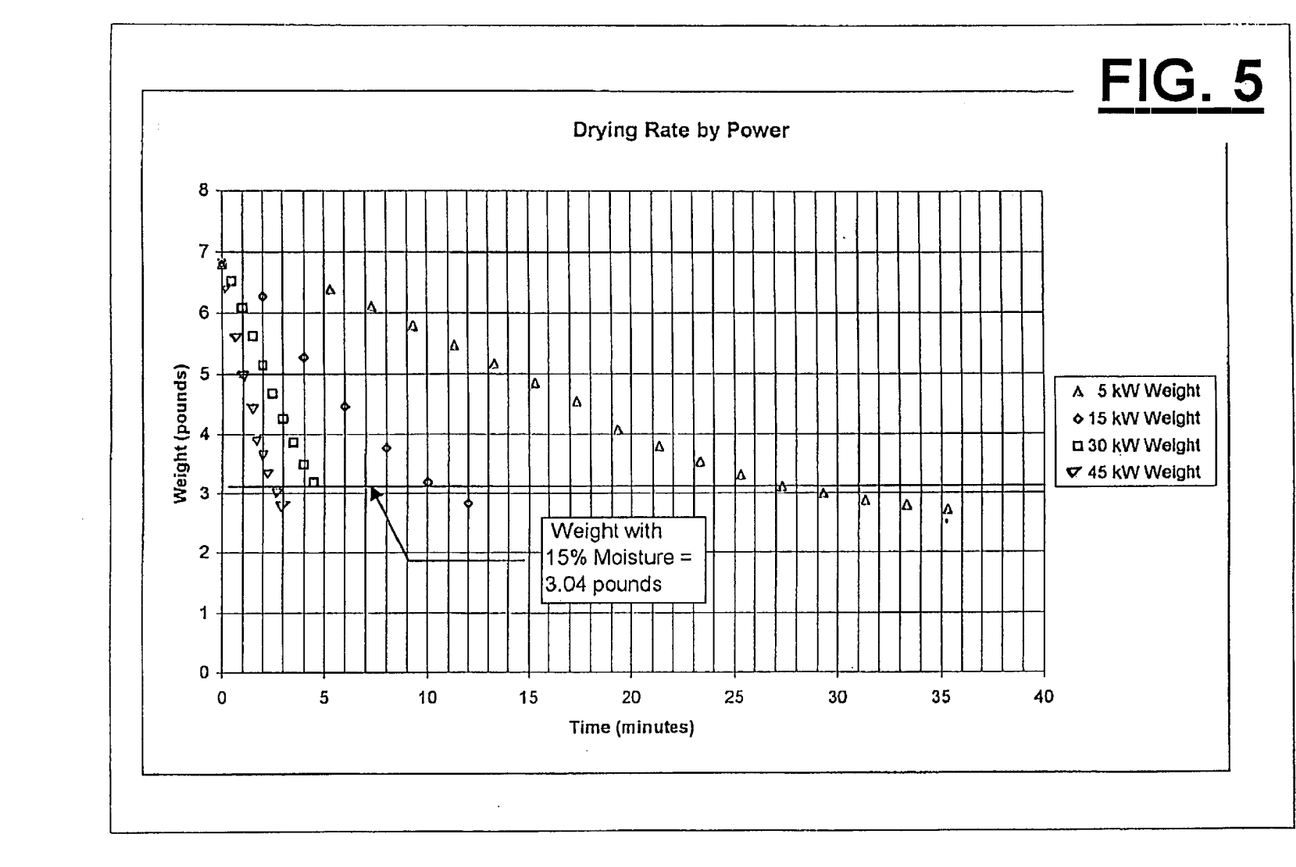
FIG. 5 is a graph illustrating drying rate by applied power vs. time.
Figure 6:
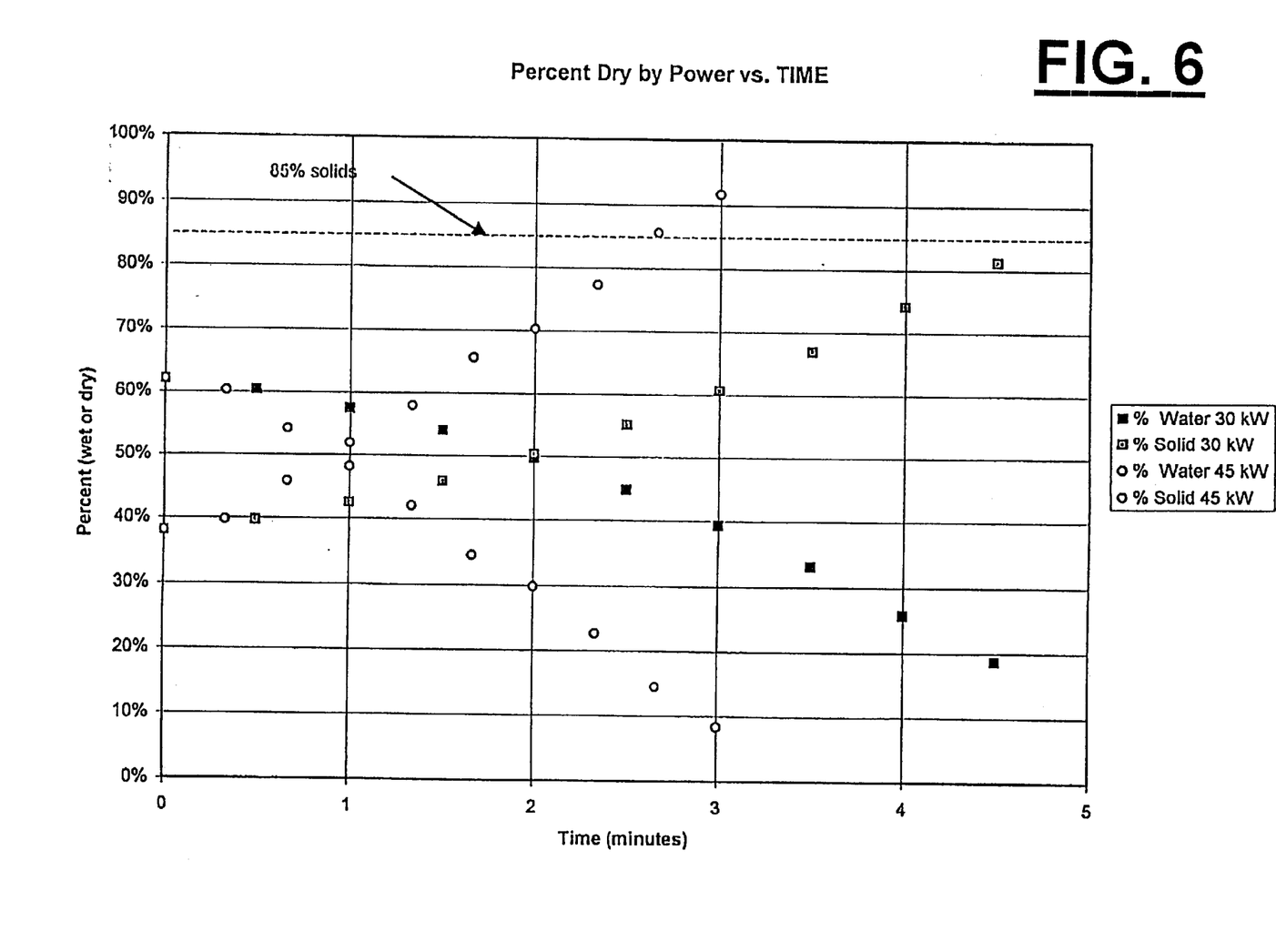
FIG. 6 is a graph illustrating moisture reduction by applied power vs. time.
Figure 7:
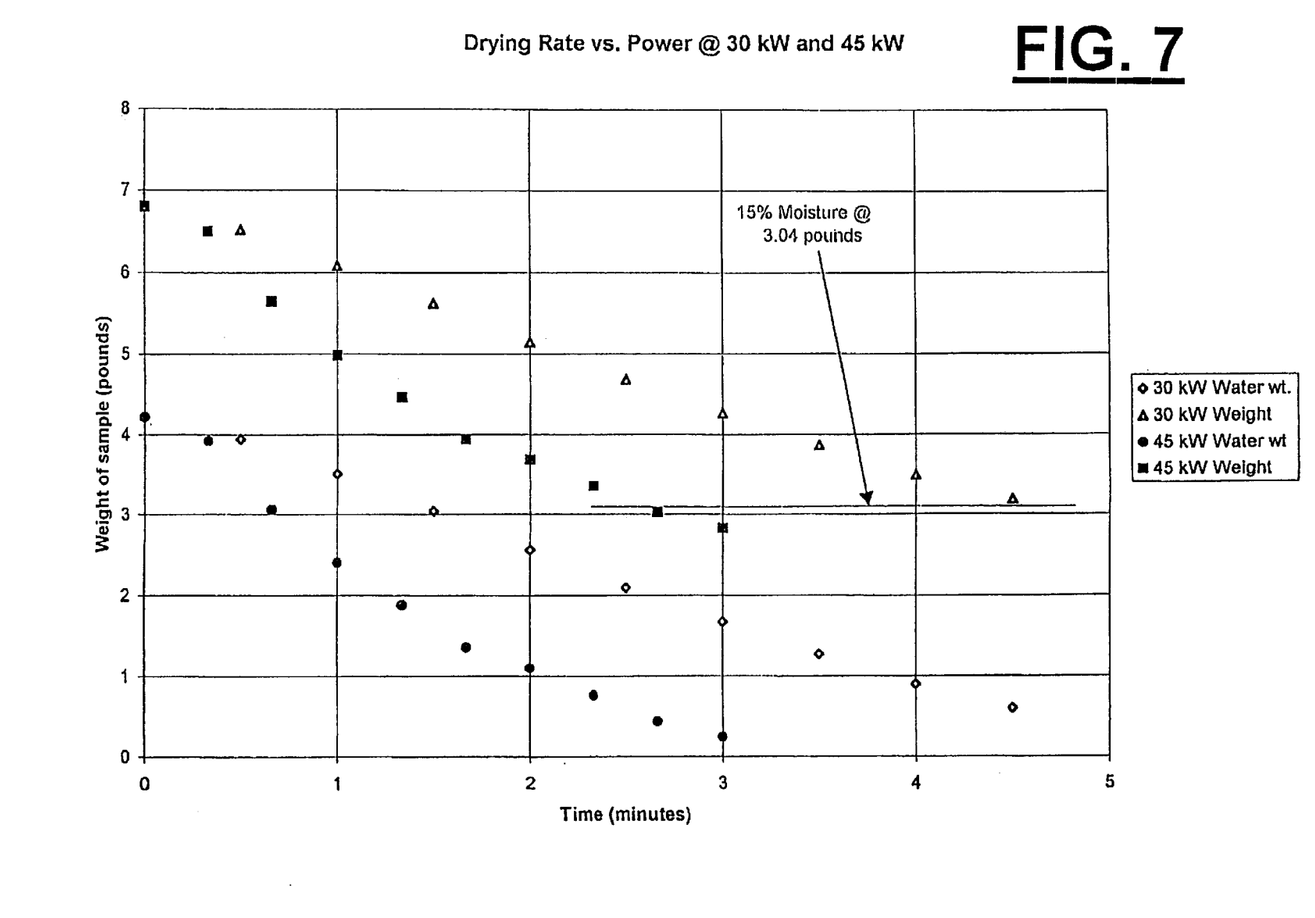
FIG. 7 is a graph illustrating drying rate vs. power at 30 kilowatts (kW) and 45 kW.

As is evident from FIGS. 5–7, drying times are reduced as power levels are increased. Moisture vs. drying time varies linearly to a first-order approximation. Drying times can be reduced exponentially by increasing microwave power as illustrated in FIG. 5. This is further illustrated in the graph comparing percent dry by power vs. time in FIG. 6, and in the graph comparing drying rate vs. power at 30 and 45 kW levels in FIG. 7.

Examples 1 and 2 were conducted with a stationary test unit described previously operating in a batch mode. The following examples were conducted with a portable microwave demonstration system containing one main control panel with PLC, controls and touchscreen, five complete 75 kW microwave generators with circulators and generator control panels, five bifurcated splitters, ten waveguide assemblies, and an applicator module containing six circulating blowers, one exhaust blower, and two complete 400,000 BTU (117.1 kW) burner assemblies with temperature monitoring and control. Material handling was accomplished by a hopper and inclined conveyor feeding a vibrating input conveyor whose output directly fed the 6' (1.8 m) wide with 2" (5.1 cm) material-retaining side rails, self-aligning, polypropylene belt traveling through the applicator at 1.75–2.00 ft/min (53.3–61.0 cm/min). This demonstration unit was invented to confirm the viability of microwave applications to potential customers prior to design of a full size, multi-module process plant. The data presented in Examples 3, 4 and 5 reflect operation in actual industrial paper producing and municipal sewage treatment plants.

EXAMPLE #3

A summary of recorded data from wet paper pulp, with a varying input moisture content from 56.84 to 66.52%, specific heat of 0.35 BTU/lb.—° F (1465.4 Joules/kg.—° C.) and density of 32.75 lbs/ft$^3$ (524.6 kg/M$^3$) is provided in Tables V–VIII. The demonstration unit was setup at the paper pulp processing section of a paper mill. The material sizes ranged from a small pebble, approximately ⅛" (0.32 cm) diameter to 1½–2¼ inches (3.8–5.7 cm) thick. The objective of the demonstration was to dry the wet paper pulp to 75–85% dry, with an input moisture of 62%. The demonstration unit was designed to continuously process 1 ton of material per hour (1814 metric tons per hour). The demonstration unit operated continuously outdoors at full power of 375 kW and full dual-burner output 800,000 BTU/hr (234.2 kW) in an ambient temperature ranging from 8°–29° F. (—13.3 to —1.7° C.). The unit continuously processed the wet paper pulp at a rate of 1.7–2.0 tons per hour (3084–3629 metric tons per hour) and achieved an output moisture content of 76.18 to 88.83%. In Examples #3–8, each burner has an associated thermocouple, positioned at the top center of the applicator, one thermocouple for over temperature protection while the other is used for process control. In this experiment, the burner temperatures remained at a constant 220° F. (104° C.) for all times.

TABLE V

(Microwave Drying of Paper Pulp)

| Parameter | Value of Parameter over time | | | | |
|---|---|---|---|---|---|
| Time | 1400 | 1500 | 1600 | 1700 | 1800 |
| Volts | 482 | 481 | 481 | 481 | 481 |
| Amperes | 776 | 892 | 886 | 875 | 879 |
| Hz | 60.0 | 60.0 | 60.0 | 60.0 | 60.0 |
| KW | 230 | 231 | 228 | 226 | 226 |
| KVAR[a] | 90 | 90 | 90 | 89 | 89 |
| Power Factor | 0.931 | 0.930 | 0.930 | 0.930 | 0.930 |
| % kW | 42.53 | 42.29 | 42.02 | 41.56 | 41.79 |
| kW-HR | 40,065 | 50,294 | 40,508 | 40,739 | 40,943 |
| Inlet water (° C.) | 12 | 12 | 12 | 12 | 12 |
| Outlet water (° C.) | 27 | 27 | 24 | 25 | 22 |
| ΔLPG (kg) | 0 | 0.5 | 0.9 | 1.1 | 1.1 |
| Belt Speed (m/min) | 0.5 | 0.5 | 0.5 | 0.5 | 0.5 |

[a]KVAR (kilovolts - amps, reactive)

In a manner similar to the previous experiment, the burner temperatures remained at a constant 220° F. (104° C.) for all times.

In this experiment, the burner temperatures ranged from 75–85° C.

TABLE VI

(Microwave Drying of Paper Pulp)

| Parameter | Value of Parameter over time | | | | | | | |
|---|---|---|---|---|---|---|---|---|
| Time | 1130 | 1230 | 1330 | 1430 | 1530 | 1630 | 1730 | 1830 |
| Volts | 480 | 480 | 480 | 480 | 480 | 480 | 480 | 480 |
| Amperes | 738 | 713 | 717 | 697 | 701 | 800 | 959 | 932 |
| Hz | 60.0 | 60.0 | 60.0 | 60.0 | 60.0 | 60.0 | 60.0 | 60.0 |
| kW | 192 | 186 | 187 | 180 | 180 | 205 | 247 | 240 |
| KVAR | 75 | 71 | 73 | 70 | 70 | 84 | 100 | 96 |
| Power Factor | 0.927 | 0.931 | 0.930 | 0.932 | 0.931 | 0.923 | 0.926 | 0.928 |
| % kW | 34.82 | 33.46 | 33.94 | 33.19 | 32.89 | 37.32 | 45.63 | 43.97 |
| kW-HR | 41,465 | 41,634 | 41,854 | 42,026 | 42,182 | 42,374 | 42,617 | 42,810 |
| Inlet water (° C.) | 12 | 12 | 12 | 12 | 12 | 12 | 12 | 12 |
| Outlet water (° C.) | 19 | 18 | 19 | 19 | 19 | 20 | 22 | 19 |
| ΔLPG (kg) | 0 | 1.0 | 2.5 | 1.5 | 1.5 | 0 | 3.0 | 1.5 |
| % Solids Out | 92.15 | 87.8 | 93.3 | 94.0 | 79.45 | 87.85 | 76.70 | 82.50 |
| Belt Speed (m/min) | 0.5 | 0.5 | 0.5 | 0.5 | 0.5 | 0.5 | 0.5 | 0.5 |

In this experiment, the burner temperatures ranged from 81–86° C.

TABLE VII

(Microwave Drying of Paper Pulp)

| Parameter | Value of Parameter over time | | |
|---|---|---|---|
| Time | 1600 | 1700 | 1800 |
| Volts | 483 | 483 | 483 |
| Amperes | 608 | 730 | 722 |
| Hz | 60.0 | 60.0 | 60.0 |
| kW | 160 | 191 | 189 |
| KVAR | 56 | 69 | 68 |
| Power Factor | 0.942 | 0.942 | 0.941 |
| % kW | 29.39 | 35.02 | 34.81 |
| kW-HR | 43,327 | 43,508 | 43,683 |
| Inlet water (° C.) | 54 | 54 | 54 |
| Outlet water (° C.) | 62 | 64 | 66 |
| Δ LPG (kg) | 0 | 1.1 | 0.5 |
| % Solids Out | 78.69 | 79.62 | 86.39 |
| Belt Speed (m/min) | 2.00 | 2.00 | 2.00 |

TABLE VIII (Microwave Drying of Paper Pulp)

| Parameter | Value of Parameter over time | | | | | | | |
|---|---|---|---|---|---|---|---|---|
| Time | 0900 | 1000 | 1100 | 1200 | 1300 | 1400 | 1500 | 1600 |
| Volts | 483 | 483 | 483 | 483 | 483 | 483 | 483 | 483 |
| Amperes | 723 | 728 | 728 | 727 | 725 | 726 | 726 | 725 |
| Hz | 60.0 | 60.0 | 60.0 | 60.0 | 60.0 | 60.0 | 60.0 | 60.0 |
| kW | 190 | 207 | 190 | 191 | 191 | 191 | 190 | 189 |
| KVAR | 68 | 77 | 69 | 69 | 69 | 69 | 69 | 68 |
| Power Factor | 0.941 | 0.938 | 0.940 | 0.940 | 0.940 | 0.941 | 0.940 | 0.941 |
| % kW | 34.82 | 37.79 | 34.87 | 35.00 | 35.02 | 35.03 | 34.99 | 34.98 |
| kW-HR | 43,850 | 44,097 | 44,238 | 44,446 | 44,640 | 44,812 | 45,004 | 45,195 |
| Inlet water (° C.) | 12.2 | 12.2 | 12.2 | 12.2 | 12.2 | 12.2 | 12.2 | 12.2 |
| Outlet water (° C.) | 18.3 | 19.4 | 17.8 | 17.2 | 18.9 | 20.0 | 19.4 | 20.0 |
| ΔLPG (kg) | 0 | 1.1 | 0.9 | 0.7 | 1.4 | 0.2 | 0.7 | 0.5 |
| % Solids In | 33.48 | 36.00 | 41.48 | 36.92 | 37.82 | 43.16 | 38.09 | 36.71 |
| % Solids Out | 74.06 | 79.44 | 88.83 | 76.18 | 80.84 | 76.29 | 84.53 | 83.40 |
| Belt Speed (m/min) | 0.6 | 0.6 | 0.6 | 0.6 | 0.6 | 0.6 | 0.6 | 0.6 |

EXAMPLE #4

A summary of recorded data from municipal and septic, treated and untreated sewage sludge with a varying input moisture content from 76–89%, specific heat of 0.12 BTU/lb.—° F. (5024.2 Joules/kg.—° C.) and average density of 62.75 lbs/ft$^3$ (1005.2 kg/lm$^3$) is provided in Tables IX–XI. The objective of the demonstration were to sufficiently reduce the pathogen count to achieve Class A material and dry the material as completely as possible. The material size ranged randomly from approximately ½" diameter to 1½" diameter balls of sewage sludge, congealed with plastic polymer. The demonstration unit was designed to continuously process 1 ton of material per hour at 62% input moisture content with 375 kW of microwave power and 800,000 BTU's/hour of combustion products of LPG. Since the plant's moisture content and minimum throughput was greater than the maximum throughput capability of the demonstration unit, the dryness objective of 20% moisture content could not be met. However, the demonstration unit still achieved a total pathogen kill, instead of only reducing the number of pathogens to the level required to achieve Class A material. Microwave units #1–5 all generated 75 kW power during the run. In this experiment, the burner temperatures ranged from 101–102° C.

TABLE IX (Microwave Drying of Biosolids)

| Parameter | Value of Parameter over time | | | | | |
|---|---|---|---|---|---|---|
| Time | 1000 | 1100 | 1200 | 1300 | 1400 | 1800 |
| Volts | 480 | 479 | 479 | 480 | 480 | 480 |
| Amperes | 928 | 954 | 948 | 954 | 930 | 918 |
| Hz | 60.0 | 60.0 | 60.0 | 60.0 | 60.0 | 60.0 |
| kW | 240 | 243 | 245 | 242 | 238 | 238 |
| KVAR | 93 | 96 | 95 | 95 | 92 | 92 |
| Power Factor | 0.932 | 0.931 | 0.930 | 0.930 | 0.932 | 0.932 |
| % kW | 44.12 | 44.71 | 44.79 | 44.06 | 43.69 | 43.89 |
| kW-HR | 5,885 | 6,137 | 6,376 | 6,613 | 6,826 | 7,066 |
| ΔkW | | 252 | 239 | 237 | 213 | 240 |
| Ambient (° C.) | 24 | 24 | 30 | 28 | 29 | 23 |
| Inlet water (° C.) | 15 | 15 | 15 | 15 | 15 | 15 |
| Outlet water (° C.) | 23 | 24 | 23 | 25 | 22 | 22 |
| ΔLPG (kg) | 0 | 0.5 | 1.1 | 0.7 | 0.2 | 0.7 |
| % Solids Out | 70 | 71 | 70 | 71 | 78 | 78 |
| Tons/hour | 2.45 | 2.49 | 2.45 | 2.49 | 2.73 | 2.73 |
| Belt Speed (m/min) | 0.5 | 0.5 | 0.5 | 0.5 | 0.6 | 0.6 |

| Pathogen Analysis | | |
|---|---|---|
| | Percent Solids | Fecal Coliforms |
| Biosolids In | 14.6% | 2.2 × 10$^5$ MPN/g |
| Biosolids Out | 38.4% | <1 MPN/g |
| Biosolids Out | 40.0% | <1 MPN/g |

As is clearly evident from the two samples which were measured, no pathogens remained in the sample.

Microwave units #1–5 all generated 75 kW power during the run. In this experiment, the burner temperatures ranged from 88–94° C.

TABLE X (Microwave Drying of Biosolids)

| Parameter | Value of Parameter over time | | | | | | | |
|---|---|---|---|---|---|---|---|---|
| Time | 0900 | 1000 | 1100 | 1200 | 1300 | 1400 | 1500 | 1530 |
| Volts | 480 | 480 | 479 | 479 | 480 | 480 | 480 | 481 |
| Amperes | 930 | 934 | 936 | 946 | 933 | 939 | 945 | 930 |
| Hz | 60.0 | 60.0 | 60.0 | 60.0 | 60.0 | 60.0 | 60.0 | 60.1 |
| KW | 240 | 242 | 242 | 243 | 240 | 242 | 243 | 240 |
| KVAR | 93 | 95 | 95 | 95 | 94 | 95 | 95 | 94 |
| P.F. | 0.932 | 0.930 | 0.930 | 0.930 | 0.931 | 0.930 | 0.930 | 0.931 |
| % kW | 44.04 | 44.57 | 44.78 | 44.42 | 44.13 | 44.63 | 44.73 | 44.18 |
| KW-HR | 7,411 | 7,655 | 7,861 | 8,096 | 8,336 | 8,577 | 8,810 | 8,931 |
| ΔkW | | 244 | 206 | 235 | 240 | 241 | 233 | 121 |
| Ambient (° C.) | 14 | 14 | 16 | 17 | 22 | 20 | 20 | 20 |
| Inlet water (° C.) | 19 | 18 | 20 | 20 | 20 | 20 | 20 | 20 |
| Outlet water (° C.) | 25 | 28 | 37 | 37 | 36 | 34 | 34 | 33 |
| ΔLPG (kg) | 0 | 1.4 | 2.7 | 0.5 | 0 | 1.4 | 0 | 0.9 |
| % Solids Out | 80 | 79 | 82 | 80 | 80 | 80 | 81 | 80 |
| Tons/hour | 2.80 | 2.77 | 2.84 | 2.80 | 2.87 | 2.80 | 2.84 | 2.80 |
| Belt Speed (m/min) | 0.6 | 0.6 | 0.6 | 0.6 | 0.6 | 0.6 | 0.6 | 0.6 |

Pathogen Analysis

| | Percent Solids | Fecal Coliforms |
|---|---|---|
| Biosolids In | 14.3% | $6.7 \times 10^4$ MPN/g |
| Biosolids Out | 43.3% | <1 MPN/g |
| Biosolids Out | 29.4% | <1 MPN/g |
| Biosolids Out | 56.9% | <1 MPN/g |
| Biosolids Out | 71.8% | <1 MPN/g |
| Biosolids Out | 52.0% | <1 MPN/g |

Microwave units #1–5 all generated 75 kW power during the run. In this experiment, the burner temperatures ranged from 91–94° C.

TABLE XI (Microwave Drying of Biosolids)

| Parameter | Value of Parameter over time | | | | | |
|---|---|---|---|---|---|---|
| Time | 0900 | 1000 | 1100 | 1200 | 1300 | 1400 |
| Volts | 480 | 480 | 480 | 480 | 480 | 481 |
| Amperes | 930 | 931 | 930 | 933 | 931 | 936 |
| Hz | 60.0 | 60.0 | 60.0 | 60.0 | 60.0 | 60.0 |
| kW | 241 | 242 | 241 | 241 | 241 | 241 |
| kVAR | 93 | 94 | 94 | 94 | 94 | 94 |
| P.F. | 0.932 | 0.931 | 0.931 | 0.931 | 0.931 | 0.931 |
| % kW | 43.96 | 44.19 | 44.17 | 44.13 | 44.29 | 44.56 |
| kW-HR | 9,333 | 9,587 | 9,828 | 10,053 | 10,305 | 10,536 |
| ΔkW | | 254 | 241 | 225 | 252 | 231 |
| Ambient (° C.) | 9 | 14 | 16 | 17 | 20 | 19 |
| Inlet water (° C.) | 15 | 15 | 15 | 15 | 15 | 15 |
| Outlet water (° C.) | 18 | 18 | 19 | 19 | 19 | 19 |
| ΔLPG (kg) | 0 | 0.9 | 0.5 | 0.5 | 0.5 | 1.4 |
| % Solids Out | 71 | 69 | 70 | 77 | 76 | 75 |
| Tons/hour | 2.49 | 2.42 | 2.45 | 2.70 | 2.66 | 2.63 |
| Belt Speed (m/min) | 0.5 | 0.5 | 0.5 | 0.6 | 0.6 | 0.6 |

EXAMPLE #5

A summary of recorded data from municipal and composted, treated and untreated sewage sludge with a varying input moisture from 73.81 to 76.49%, specific heat of 0.18 BTU/lb and average density of 66.1 lbs/ft³ is provided in Table XII. The objectives of the demonstration were to sufficiently reduce the pathogen count to achieve Class A material and dry the material as completely as possible. The material size ranged randomly from approximately ¾ inch diameter to ½ inch diameter balls of sewage sludge, congealed with plastic polymer. The demonstration unit was designed to continuously process 1 ton of material per hour at 62% input moisture content, with 375 kW of microwave power and 800,000 BTU/hour of combustion products of LPG. Since the plant's moisture content and minimum throughput was greater than the maximum throughput capability of the demonstration unit, the dryness objective of 20% moisture content could not be met.

However, the demonstration unit still achieved a total pathogen kill, instead of only reducing the number of pathogens to the level required to achieve Class A material. Microwave units #1–5 all generated 75 kW power during the run. In this experiment, the temperature below the belt, as measured approximately 2' (0.6 m) in from each side (inlet/exit) and measured the temperature below the moving belt, ranged from 74–125° C.

TABLE XII

(Microwave Drying of Biosolids)

| Parameter | Value of Parameter over time | | | | | | |
|---|---|---|---|---|---|---|---|
| Day # | 1 | 1 | 1 | 1 | 2 | 3 | 3 |
| Time | 1200 | 1300 | 1400 | 1500 | 1545 | 1200 | 1300 |
| Volts | 480 | 480 | 480 | 480 | 483 | 480 | 483 |
| Amperes | 600 | 600 | 600 | 600 | 625 | 600 | 600 |
| Hz | 60.0 | 60.0 | 60.0 | 60.0 | 60.0 | 60.3 | 60.3 |
| KW | 475 | 475 | 475 | 475 | 500 | 475 | 475 |
| B1-TC1 (° C.) | 102 | 101 | 103 | 103 | 94 | 102 | 101 |
| B2-TC2 (° C.) | 98 | 98 | 99 | 98 | 89 | 97 | 97 |
| B1-TC3 (° C.) | 102 | 101 | 102 | 102 | 93 | 101 | 100 |
| B2-TC4 (° C.) | 101 | 101 | 101 | 102 | 93 | 100 | 101 |
| Moisture In | 23.74 | 23.69 | 23.64 | 24.21 | 26.19 | 25.10 | 25.18 |
| Moisture Out | 34.36 | 32.50 | 36.99 | 43.10 | 37.73 | 47.72 | 53.40 |
| Ambient (° C.) | 27 | 28 | 29 | 31 | 29 | 28 | 32 |
| Inlet water (° C.) | 15 | 16 | 16 | 16 | 16 | 16 | 16 |
| Outlet water (° C.) | 22 | 22 | 22 | 20 | 21 | 22 | 22 |
| Δ LPG (kg) | 0 | 0.9 | 0.5 | 0 | 3.6 | 1.8 | 0.9 |
| % Solids Out | 61 | 60 | 57 | 56 | 52 | 52 | 51 |
| Belt Speed (m/min) | 0.8 | 0.8 | 0.6 | 0.6 | 0.7 | 0.7 | 0.7 |

Pathogen Analysis

| | Percent Solids | Fecal Coliforms |
|---|---|---|
| Biosolids In | 29.6% | $3.2 \times 10^6$ MPN/g |
| Biosolids Out | 37.9% | <1 MPN/g |
| Biosolids Out | 46.5% | <1 MPN/g |
| Biosolids Out | 51.9% | <1 MPN/g |
| Biosolids Out | 36.0% | <1 MPN/g |
| Biosolids Out | 47.2% | <1 MPN/g |
| Biosolids Out | 47.3% | <1 MPN/g |
| Biosolids Out | 39.4% | <1 MPN/g |

While the discussion has focused primarily on organic drying applications, there is no need to limit to such. One outgrowth of this technology is that concurrent with moisture reduction, pathogen reduction is simultaneously occurring. In past years, processing Class "A" biosolids has been reliant on natural Gas and Liquid Petroleum Gas (LPG) fired drum dryers and vertical chamber incinerators which at best, are 60% efficient. The cost involved in owning and operating these methods have made it practically impossible for waste water facilities to process Class "A" biosolids, whereas the Microwave Thermal Process operates at an efficiency rate of 85%. If waste water biosolids or sludge can be treated to meet Class "A", Alternative "6," (40 CFR 503) the generators or waste water facilities can do anything with the end product, such as: give biosolids away, or market the biosolids without any restrictive regulations. The microwave thermal process not only completes a total pathogen kill, but also reduces the amount of moisture content, which results in less tonnage to be removed form the facilities.

In fact, it is envisioned that both decrosslinking and depolymerization reactions are contemplated and within the scope of this invention. In one such embodiment, waste organic materials, such as scrap tires, are gasified by the application of microwave and convection energy using a continuous, self-aligning, porous, 6' (1.82 m) wide stainless steel 304/316 type belt with 2" (5.08 cm) material retaining sides and 24–28% open area, to produce a stable product which comprises essentially ethane and methane.

When the invention is used in this mode, a process is provided for the recovery of specified gaseous products and includes maintaining the gas stream at a temperature at least as high as an equilibrium temperature above which the specified products are thermodynamically favored, followed by quickly cooling the gas stream to a temperature at which the specified products are stabilized.

When gasifying tires, the preferred gaseous product is a gas stream which consists of substantially of ethane and methane in a ratio of two parts ethane to one part methane by weight. A product stream which various from the preferred range, but which is also acceptable comprises ethane, methane and propane at substantially 50% by weight ethane and 25% by weight of each of methane and propane. Mixtures of ethane/methane have very high heat values and can be burned directly without further treatment in some instances.

Preferably, the tires are shredded, although this is not necessary. If shredded, the chips are fed sequentially to a washer and a dryer and then to the microwave chamber. Solid carbon products of the microwave process are withdrawn and fed to a carbon/steel separator. The gas stream emanating from the microwave chamber is sampled and analyzed by gas chromatograph. The gas stream is typically fed through a filter to remove any larger particles which may become entrained in the stream and also through a subsequent filter to remove any fine entrained particles. When the feedstock contains sulfur, a scrubber is used to permit the effective removal of the sulfur. Exiting gas is fed through a flash cooler, followed by feeding through a compressor and nitrogen rejection unit, preferably a molecular sieve. This results in increased gas concentration and nitrogen recovery.

Conditions within the microwave applicator, tunnel or chamber are chosen so as to produce the desired components in the gas stream. In a preferred embodiment, no liquid products, e.g., oils, will be produced. In order to insure that a 2:1 ratio of ethane:methane is produced, the feed rate, residence time and energy level from the magnetrons is controlled as well as the temperature within the applicator, tunnel or chamber.

In a typical rubber tire reduction case, the following conditions will produce the desired ethane:methane mix. The preferred applicator will contain anywhere from 3 to 10 modules of from 3 to 7, preferably 5 magnetrons, each magnetron operating at about 915 MHz. Under these conditions, at steady state operation, a residence time of the gaseous stream in the tunnel of approximately 300 milliseconds will result in a temperature in the tunnel of about 572° F. (300° C). Typically, the process pressure will range from 0.1 to 0.5 psig (0.7 to 3.4 kPa). As kinetics favor reactions below equilibrium, the intermediate reactions release free hydrogen, which furthers the reduction of more complex organic molecules, leading to further breakdown and a higher rate of reduction. The chemical reactions are exothermic in nature.

For crosslinked styrene butadiene rubbers (SBR), the production of gaseous product comprises the initial depolymerization of the sulfur crosslinks followed by the addition of further microwave energy over time resulting in the breakdown of the two main polymers to form the desired products. At temperatures above about 572° F. (300° C.), depending on the feed stock, thermodynamics favor methane and ethane over the original polymers or other polymers. Accordingly, once depolymerization is complete by maintaining those temperatures and applying the requisite microwave energy over a required period of time, the gas stream remains stable at the high temperature. Very rapid cooling will prevent repolymerization or recombination of the gas constituents. The gas stream is scrubbed of sulfur, preferably in a dry-contact, top-fed packed tower packed with limestone and dolomite, while maintaining the gas temperature above the equilibrium point. The gas is then flash cooled, preferably down to about 100° F. (38° C.), to stabilize the ethane and methane at the lower temperatures. The residence time of the gas stream in the tunnel is controlled in large part by a compressor used in the supplemental convection heat flow.

A blanketing gas is often used, nitrogen and argon being the two preferred gases. This gas may be supplied through drilled orifices through the choke pins in each R. F. trap. Nitrogen is often preferred due to its lower cost, but has the potential of reacting with aromatic gaseous products, e.g., isomers of xylene, benzene, toluene, etc., at the temperatures involved, thereby forming undesirable and environmentally unfriendly NOX products. This requires catalytic post processing with hydrogen and zeolites. Alternatively, argon can be used at higher cost, although lowered amounts are typically required due to its higher molecular weight.

Discussion

Without being held to one theory of operation, or one mode of performance, it is believed that the benefits of the invention are derived at least in part, by introducing microwave excitation of water molecules inside the organic material by subjecting the material to high frequency radiowaves in the ultra-high frequency (UHF) band. The polar water molecules in the material attempt to align themselves with the oscillating electric field at a frequency of 915 MHz or approximately every nanosecond. As the molecules cannot change their alignment synchronously with the changing electric field, the resistance to change manifests itself as heat and the moisture trapped within the material is released as water vapor. The heated air flowing though the material converts any surface moisture to water vapor. This efficient release of moisture from the organic material reduces energy costs ~30%, increases throughput ~25%, reduces plant layout space ~75%, reduces installation time ~85% and reduces the number of operating personnel. As the invention is designed for unattended, automatic operation, with a display in the customer's main control room, no additional personnel are required. The use of this invention results in an immediate increase in drying efficiency from ~60% with conventional gas dryers to ~85% employing the combination of microwave and convection oven technologies.

However, in the case of tires and plastics, a phenomenon known as thermal runaway occurs due to the inability of these materials to dissipate the internal heat caused by microwave excitation sufficiently fast to their surroundings. Therefore, the rate of increase in enthalpy is greater within the material than in the surrounding region. The internal temperature continues to increase at an even faster rate and decomposition subsequently occurs. With a high density electric field, metal particles within the material and a higher loss factor after decomposition begins, the products of decomposition have an even higher loss factor. Since the loss factor is proportional to the power density and a rise in temperature, the material is subjected to even higher internal power dissipation. As carbon is one of the intermediate products of high-temperature decomposition and has much higher loss factor than plastics or rubber, the higher temperature leads to even greater power dissipation within the material, leading to further molecular breakdown. Hydrogen released during the molecular breakdown and the thermal runaway phenomenon produce an intense series of exothermic reactions, until equilibrium occurs. Thermodynamic control is favored above equilibrium.

Raw Material Particle Sizing Aspects

The starting material for this invention is typically in a chunk form, a diameter or thickness of which typically does not exceed 2 inches. This is due to the recognition that the penetration depth of the microwaves at this power is typically about 2 inches. The minimum size consideration is dependent upon the physical mesh of the belt, and minimum physical weight constraints so that the material does not become entrained within the gas convection heating gas(es) and become blown through the exit portals. The conveyor belt typically has material retaining sides which are dimensioned so as to at least accommodate the penetration depth of the microwaves.

Contact Time

The contact time of the material within the chamber is primarily dependent on the speed of the belt, which is controlled by a variable speed motor, which in a typical application will range from 1 to 8 feet/minute. Increasing the contact time within the chamber will increase the degree of dryness associated with the sample. Increasing the contact time still further, will result in bond breaking, leading to either decrosslinking or depolymerization or both, occurring either simultaneously or sequentially, dependent on the energy associated with the microwaves.

Waveguide Orientation

In a preferred embodiment, the waveguides will be bifurcated and positioned at 90° with respect to the X and Y axes. In this orientation, the microwaves will be essentially out of phase with respect to each other. Through experimentation, it was determined that the most even microwave density was produced using this configuration without going to the arc-over point or the voltage breakdown point.

Microwave Frequency

Historically, the frequency of 915 MHz was not originally allocated for use in the Industrial, Scientific and Medical (ISM) applications throughout the world, and no allocation for 915 MHz applications exists today in continental Europe. In addition, only low power magnetrons (<3 kW) were available for 2450 MHz use, but 15–60 kW magnetrons were readily available for 915 MHz use. Currently, magnetron selection from 2.2–30 kW exist at 2450 MHz, while magnetrons operating at 915 MHz are available from 10–200 kW. The preferred frequency of operation for this invention was chosen primarily for increased penetration depth, increased power availability and reduced number of magnetrons required per chamber. The use of magnetrons operating at 915 MHz and a power level of 75 kW results in the most cost effective design for today's applicators. These magnetrons are most readily available from stock, should replacement be required.

Pathogen Destruction

The invention mechanically and biologically introduces microwave excitation of water molecules inside the biosolids material by subjecting the material to high frequency radio waves in the ultra-high frequency (UHF) band. The pathogens and polar water molecules in the material attempt to align themselves with the oscillating electric field at a frequency of 915 MHz or approximately every millisecond. The pathogens or molecules within the pathogens cannot align themselves synchronously, creating an atmosphere of excitement, which causes heat and explodes the pathogens structurally.

At this point of excitement, not only do the pathogens self-destruct, the attached water molecules of the pathogens release the moisture as water vapor. The chamber is already heated to 106° C., which allows the vapor to rise with the help of induction and exhaust fans and removes vapor from biosolids material out into the atmosphere. Once the biosolid material has exited the microwave chamber, all pathogens have been destroyed and the material no longer has a vector attraction. This result, not only meets but also exceeds all requirements for Class A, Alternative "6" of 40 C.F.R., Part 503 specification for Process to Further Reduce Pathogens (PFRP).

The best mode for carrying out the invention has been described for the purposes of illustrating the best mode known to the applicant at the time. The examples are illustrative only and not meant to limit the invention, as measured by the scope and spirit of the claims. The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A process for drying which comprises the steps of:
   (a) feeding a sample containing water onto a mesh conveyor belt leading into at least one microwave applicator;
   (b) exposing said sample in said microwave applicator to at least two sources of microwaves, said microwaves being in non-parallel alignment to each other; and
   (c) collecting said sample after exiting from said at least one chamber.
2. The process of claim 1 wherein
   (a) said step of exposing said sample occurs in at least one heated chamber having an air flow about said sample.
3. The process of claim 1 wherein
   (a) said at least two sources of microwaves are from a split waveguide assembly.
4. The process of claim 3 wherein
   (a) said split waveguide assembly introduces microwaves into said applicator which are essentially 90° out of phase to each other.
5. The process of claim 2 wherein
   (a) said at least one heated chamber is between approximately 75° C. and 125° C.
6. The process of claim 5 wherein
   (a) said heated chamber is heated by a heating means selected from the group consisting of electric resistance heating, infra-red, quartz lamp, natural gas burning, liquefied petroleum gas burning, and combinations thereof.
7. The process of claim 1 wherein
   (a) a frequency of said microwaves is between 915 MHz and 1000 MHz.
8. The process of claim 7 wherein
   (a) said frequency is approximately 915 MHz.
9. The process of claim 4 wherein
   (a) said sample for feeding is sewage.
10. The process of claim 9 wherein
    (a) analysis of said sample subsequent to collecting has a density of fecal coliform in said sample of less than one most probable numbers per gram total solids on a dry weight basis.
11. The process of claim 4 wherein
    (a) said sample is a polymer which is at least partially depolymerized or decrosslinked.
12. The process of claim 11 wherein
    (a) said sample is a tire.
13. A process which comprises:
    (a) feeding a sample containing water onto a mesh conveyor belt leading into at least one microwave applicator;
    (b) exposing said sample in said microwave applicator to microwaves which are out of phase with respect to each other; and
    (c) collecting said sample after exiting from said at least one chamber.
14. The process of claim 13 wherein
    (a) said step of exposing said sample occurs in at least one heated chamber having an air flow about said sample.
15. The process of claim 13 wherein
    (a) said microwaves emanate from at least two sources of microwaves in a split waveguide assembly.
16. The process of claim 15 wherein
    (a) said split waveguide assembly introduces microwaves into said applicator which are essentially 90° out of phase to each other.
17. The process of claim 14 wherein
    (a) said at least one heated chamber is between approximately 75° C. and 125° C.
18. The process of claim 17 wherein
    (a) said heated chamber is heated by a heating means selected from the group consisting of electric resistance heating, infra-red, quartz lamp, natural gas burning, liquefied petroleum gas burning, and combinations thereof.
19. The process of claim 13 wherein
    (a) a frequency of said microwaves is between 915 MHz and 1000 MHz.
20. The process of claim 19 wherein
    (a) said frequency is approximately 915 MHz.
21. The process of claim 16 wherein
    (a) said sample for feeding is sewage.
22. The process of claim 21 wherein
    (a) analysis of said sample subsequent to collecting has a density of fecal coliform in said sample of less than 1 most probable numbers per gram total solids on a dry weight basis.

23. The process of claim 16 wherein
(a) said sample is a polymer which is at least partially depolymerized or decrosslinked.

24. The process of claim 23 wherein
(a) said sample is a tire.

25. A process which comprises:
(a) feeding a sample containing water onto a mesh conveyor belt leading into at least one microwave applicator;
(b) exposing said sample in said microwave applicator to microwaves which enter said chamber in at least two planes at a top of said applicator; and
(c) collecting said sample after exiting from said at least one chamber.

26. The process of claim 25 wherein
(a) said step of exposing said sample occurs in at least one heated chamber having an air flow about said sample.

27. The process of claim 25 wherein
(a) said microwaves emanate from at least two sources of microwaves in a split waveguide assembly.

28. The process of claim 27 wherein
(a) said split waveguide assembly introduces microwaves into said applicator which are essentially 90° out of phase to each other.

29. The process of claim 26 wherein
(a) said at least one heated chamber is between approximately 75° C. and 125° C.

30. The process of claim 29 wherein
(a) said heated chamber is heated by a heating means selected from the group consisting of electric resistance heating, infra-red, quartz lamp, natural gas burning, liquefied petroleum gas burning, and combinations thereof.

31. The process of claim 25 wherein
(a) a frequency of said microwaves is between 915 MHz and 1000 MHz.

32. The process of claim 31 wherein
(a) said frequency is approximately 915 MHz.

33. The process of claim 28 wherein
(a) said sample for feeding is sewage.

34. The process of claim 33 wherein
(a) analysis of said sample subsequent to collecting has a density of fecal coliform in said sample of less than 1 most probable numbers per gram total solids on a dry weight basis.

35. The process of claim 28 wherein
(a) said sample is a polymer which is at least partially depolymerized or decrosslinked.

36. The process of claim 35 wherein
(a) said sample is a tire.

* * * * *